United States Patent [19]

Carrico

[11] Patent Number: 4,833,084
[45] Date of Patent: May 23, 1989

[54] MONOCLONAL ANTIBODY SPECIFIC FOR DNA·RNA HYBRIDS

[75] Inventor: Robert J. Carrico, Elkhart, Ind.

[73] Assignee: Miles Inc., Elkhart, Ind.

[21] Appl. No.: 769,022

[22] Filed: Aug. 26, 1985

Related U.S. Application Data

[63] Continuation-in-part of Ser. No. 707,420, Mar. 1, 1985, abandoned, which is a continuation-in-part of Ser. No. 616,132, Jun. 1, 1984, abandoned.

[51] Int. Cl.⁴ .................. C12N 5/00; C07K 15/06; C12Q 1/68; C12P 21/00
[52] U.S. Cl. .................... 435/240.27; 435/6; 435/7; 435/68; 530/387; 935/78; 436/548
[58] Field of Search .............. 435/6, 7, 948, 240.27, 435/68, 948; 530/387; 436/501, 508, 512, 548; 935/78, 103

[56] References Cited

U.S. PATENT DOCUMENTS

| | | | |
|---|---|---|---|
| 4,358,535 | 11/1982 | Falkow et al. | 435/5 |
| 4,376,110 | 3/1983 | David et al. | 435/7 X |
| 4,732,847 | 3/1988 | Stuart et al. | |
| 4,743,535 | 5/1988 | Carrico | 435/6 |

OTHER PUBLICATIONS

Stuart, W. D. et al., *Proc. Natl. Acad. Sci. U.S.A.*, vol. 78, No. 6 1981, pp. 3751–3754.

St. Groth, S. In Handbook of Monoclonal Antibodies (Ferrone, S. et al. ed.) Noyes Publications, New Jersey, 1985, p. 7.

*Primary Examiner*—Ronald W. Griffin
*Assistant Examiner*—Jeremy M. Jay
*Attorney, Agent, or Firm*—Andrew L. Klawitter

[57] ABSTRACT

A monoclonal antibody specific for DNA·RNA duplexes, particularly DNA·RNA heteropolymer duplexes, characterized by having cross-reactivity for binding to single- or double-stranded DNA or RNA as measured by competitive immunoassay of less than about 1:1000, and preferably less than 1:10,000, and an affinity for DNA·RNA heteropolymer duplexes greater than $10^9$ L/mole. The monoclonal antibody is prepared by conventional somatic cell hybridization techniques wherein the host animal is preferably immunized with an immunogen comprising a random DNA·RNA heteropolymer. The antibody, particularly in a labeled form, is useful in the specific detection of DNA·RNA duplexes in a test medium such as a nucleic acid hybridization assay mixture.

2 Claims, 2 Drawing Sheets

MONOCLONAL ANTIBODY SPECIFIC FOR DNA·RNA HYBRIDS

CROSS REFERENCE TO RELATED APPLICATIONS

This is a continuation-in-part application of application Ser. No. 707,420, filed Mar. 1, 1985, which is a continuation-in-part application of application Ser. No. 616,132, filed June 1, 1984 both abandoned.

BACKGROUND OF THE INVENTION

This invention relates to the preparation of antibodies, particularly monoclonal antibodies secreted by somatic cell hybridomas, to nucleic acids, particularly DNA·RNA hybrids. Such antibodies are useful in the isolation, detection, and quantitation of nucleic acid duplexes. In particular, the antibodies can be used in nucleic acid hybridization assays to detect hybrids formed between a polynucleotide sequence of interest in a test sample and a known complementary probe.

The detection of specific polynucleotide sequences by the analytical hybridization technique is useful in the fields of recombinant DNA, human and veterinary medicine, agriculture, and food science, among others. In particular, the technique can be used to detect and identify etiological agents such as bacteria and viruses, to screen bacteria for antibiotic resistance, to aid in the diagnosis of genetic disorders such as sickle cell anemia an thalassemia, and to detect cancerous cells.

The state-of-the-art nucleic acid hybridization assay techniques generally involve immobilization of the sample nucleic acid on a solid support followed by hybridization with a labeled form of a complementary probe polynucleotide. Hybridization between particular base sequences or genes of interest in the sample nucleic acid and labeled probe is determined by separating the solid support from the remainder of the reaction mixture which contains unbound labeled probe, followed by detection of the label on the solid support. The preparation of labeled probe generally involves chemical modification of the probe nucleic acid to attach or form a detectable chemical group.

The necessity of immobilizing sample nucleic acids and/or chemically modifying the probe in order to perform conventional hybridization methods poses several significant problems. The procedures required to accomplish immobilization are generally time consuming and add a step which is undesirable for routine use of the technique in a clinical laboratory. Proteins and other materials in the heterogeneous sample, particularly in the case of clinical samples, can also interfere with the immobilization of the nucleic acids. Further, the large-scale preparation of labeled probes normally involves complicated and expensive synthetic and purification procedures. Because the labeled polynucleotide must retain its ability to sensitively hybridize with its complementary sequence of interest, the availability of useful synthetic approaches is severely limited. The synthesis of labeled probes by the methods of nick translation, end labeling, second strand synthesis, and reverse transcription involve enzymatic steps which add the further requirement that the modified or labeled nucleotides must serve as effective substrates for the polymerase enzymes that assemble the labeled polynucleotide. Direct chemical modification of the polynucleotide is also possible, however, such methods are generally quite inefficient and can alter the ability of the labeled polynucleotide to hybridize to the complementary sequence.

As alternatives to immobilizing sample nucleic acids and adding labeled probe, one can use an immobilized probe and label the sample nucleic acids in situ, or one can use a dual hybridization technique requiring two probes, one of which is immobilized and the other labeled [*Methods in Enzymology* 65:468 (1968) and *Gene* 21:77–86 (1983)]. The former alternative, however, is even less desirable since the in situ labeling of the sample nucleic acids requires a high degree of technical skill which is not routinely found in clinical technicians and there are no simple, reliable methods for monitoring the labeling yield, which can be a significant problem if the labeling media contain variable amounts of inhibitors of the labeling reaction. The dual hybridization technique has the disadvantages of requiring an additional reagent and incubation step and the kinetics of the hybridization reaction can be slow and inefficient. The accuracy of the assay can also be variable if the complementarity of the two probes with the sample sequence is variable.

Techniques for directly detecting the polynucleotide duplex formed as the product of hybridization between the sample and probe polynucleotides, and thereby dispensing with the chemical labeling and immobilization of sample or probe polynucleotides, have been generally unsatisfactory. Attempts to generate antibodies which will selectively bind double stranded DNA hybrids over single stranded DNA have generally failed [Parker and Halloran, "Nucleic Acids in Immunology", ed. Plescia and Braun, Springer-Verlag, (New York 1969) pp. 18 et seq]. However, there is a recent report of a monoclonal antibody specific for double stranded native DNA with no indication as to its affinity (European Patent Publication No. 135,159). Hybridization formats are described which in principle eliminate the need for chemical modification of probe DNA for labeling purposes. These methods will suffer from high background signal due to immobilization of nonspecific ds-DNA which is ubiquitous in most test samples and in hybridization solutions.

Some success has been achieved in generating polyclonal antibodies that will bind DNA·RNA mixed hybrids or RNA·RNA hybrids and have low affinity for the single stranded polynucleotides [see, for example, Rudkin and Stollar, *Nature* 265:472 (1977); Van Prooijen-Knegt et al., *Exp. Cell Res.* 141:397(1982); Reddy and Sofer, *Biochem. Biophys. Res. Commun.* 103:959 (1981); and Nakazato, *Biochem.* 19:1835 (1980)].

The polyclonal antiserums contain antibodies to single stranded polynucleotides and double stranded RNA as well as antibodies to DNA·RNA duplexes. Pure antibody specific for DNA·RNA would have to be isolated from antiserum or fractionated antiserum by immunoadsorption which is practical only on a small scale. Preparations obtained by immunoadsorption would usually contain immunoglobulins which would not bind DNA·RNA and these reduce the quality of labeled antibody preparations. These preparations also would contain a mixture of antibodies with various affinities. The quality of antibodies obtained would vary between bleedings from one animal and among antiserums from different animals.

Monoclonal antibody technology can provide a means to select an antibody with desired affinity and specificity. Since hybridomas can be preserved and propagated for long periods, the reproducibility of antibody quality is assured. Stuart et al., PNAS (USA) 78:3751 (1981) immunized mice with a poly(A)·poly(dT) duplex and isolated a hybridoma that produced an antibody to DNA·RNA. No data is provided concerning the specificity of this monoclonal antibody or its affinity for various DNA·RNA duplexes. Since it was prepared against a DNA·RNA homopolymer [poly(A)·poly(dT)], it would be expected to have significantly less specificity and affinity for DNA·RNA heteropolymer duplexes.

SUMMARY OF THE INVENTION

The present invention provides a monoclonal antibody that is highly specific and has high affinity for binding to DNA·RNA hybrids, particularly DNA·RNA heteropolymer duplexes. The cross-reactivity of the monoclonal antibody for binding to single- or double-stranded DNA or RNA, as measured by competitive immunoassay, is less than about 1:1000, and preferably less than about 1:10,000. Affinity for binding DNA·RNA heteropolymer duplexes, expressed in terms of an association constant, is greater than about $10^9$ L/mole, and preferably greater than about $10^{10}$ L/mole.

The antibody is obtained from the secretions of a somatic cell hybridoma prepared by conventional techniques. A selected host animal is immunized with an immunogen comprising a DNA·RNA duplex, preferably a random DNA·RNA heteropolymer, lymphocytes from the animal secreting antibodies to DNA·RNA are fused with myeloma cells to produce hybridomas which are cloned to isolate one or more that secrete specific antibodies, and the isolated hybridoma or hybridomas are subcloned to assure monoclonality of the secreted antibody.

DNA·RNA duplexes can be determined in a suitable test medium by contact wit the present monoclonal antibody and determination of the amount of antibody that binds to the DNA·RNA duplexes in the test medium. A variety of assay formats are made possible for detecting specific polynucleotide sequences by forming hybrids with the probe which are DNA·RNA duplexes and determining such duplexes by means of specific binding to the present antibody. Normally, the antibody will be immobilized, or immobilizable, or labeled in order to permit convenient detection of the immune complex.

The present invention also provides continuous hybridoma cell lines that secrete the anti-DNA·RNA monoclonal antibody, and the use thereof to prepare the antibodies of the present invention.

DESCRIPTION OF THE PREFERRED EMBODIMENTS

Figure 1:
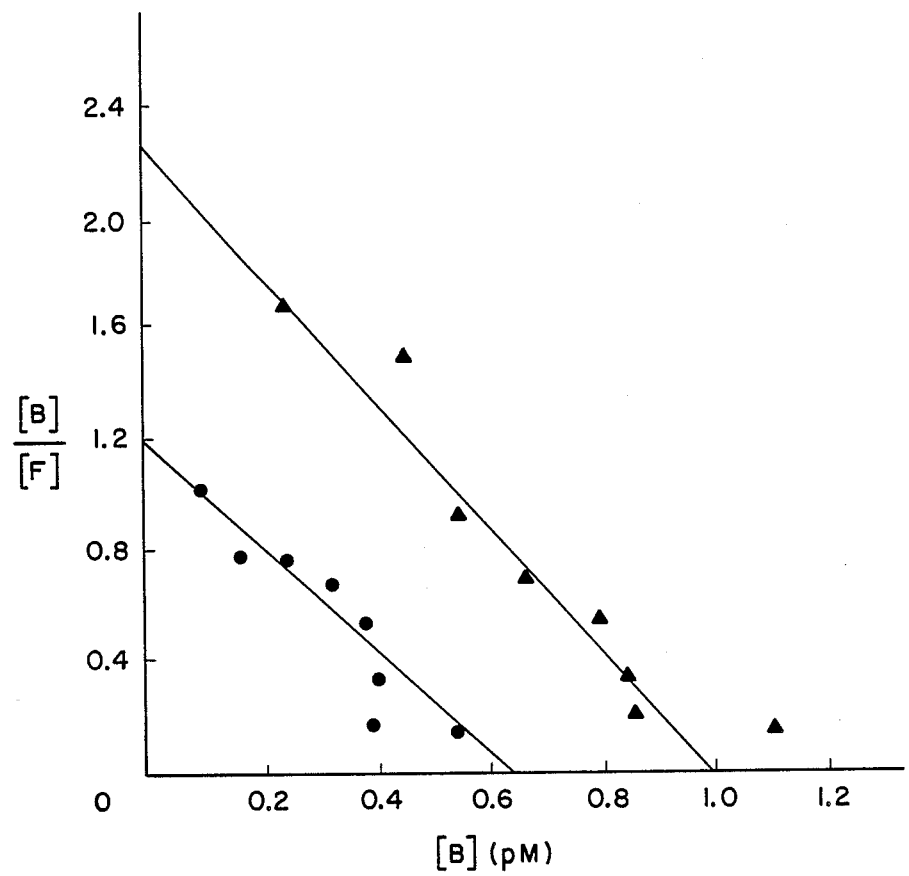
FIG. 1 is a Scatchard plot for the binding of DNA·RNA by a monoclonal antibody of the present invention. Details are provided in Example II.

When referring to the antibody of the present invention it is intended to include whole, intact antibodies, antibody fragments, polyfunctional antibody aggregates, or in general any antibody-derived substance that comprises at least one antibody combining site having the characteristics described herein. Antibodies of any of the known classes and subclasses of immunoglobulins are contemplated, e.g., IgG, IgM, and so forth, as well as active fragments such as the IgG fragments conventionally known as Fab, F(ab'), and F(ab')$_2$.

The present monoclonal antibody is characterized by a high degree of specificity for DNA·RNA duplexes. Antibody specificity is the capacity of an antibody to bind the corresponding antigen to the relative exclusion of other substances, particularly substances having closely related molecular structures. A critical property of an antibody intended for use in detecting antigen is its ability to exclude binding of related substances that might appear in the test medium. In the case of detection of DNA·RNA duplexes, the antibody should bind strongly to DNA·RNA, particularly its random heteropolymeric forms, but essentially not at all to biologically important mononucleotides and polynucleotides, particularly single- and double-stranded DNA and RNA. The present antibody is characterized by at least about $10^3$, and preferably greater than about $10^4$, greater affinity for DNA·RNA duplexes than other single-stranded or double-stranded nucleic acids. Preferably, the antibody shows strongest affinity for DNA·RNA heteropolymers irrespective of base sequence, however, strong binding to DNA·RNA homopolymers is also observed but is of no consequence for most analytical applications.

A variety of methods are known for measuring antibody specificity. Competitive binding measurements are sensitive means for determining cross-reactivity of an antibody to substances other than the antigen of interest. Typically, a labeled form of the antigen of interest is used with a level of antibody that will bind between about 40 to 60 percent of the antigen present. A fixed level of the labeled antigen and various levels of a potential cross-reacting substance are incubated with the antibody until equilibrium is reached. Bound or free labeled antigen is then measured and cross-reaction will be indicated by a decrease in the level of labeled antigen bound to antibody as the amount of cross-reactant is increased. Cross-reactivity can then be expressed as the ratio of the amount of antigen required to displace 50 percent of the labeled antigen from the antibody to the amount of cross-reactant required to do the same. The present antibody shows cross-reactivity for binding to single- or double-stranded DNA or RNA, as measured by this competitive immunoassay technique, of less than about 1:1000, and commonly less than about 1:10,000 (see the examples below and the results shown in FIG. 2). Moreover, the present antibody shows cross-reactivity for binding to the homopolymeric DNA·RNA duplex represented by poly(A)·poly(dT) of less than about 1:100.

Monoclonal antibodies of the present invention are harvested from the secretions of hybridoma cells produced by somatic cell hybridization techniques originating from the work of Kohler and Milstein, Nature 256:495 (1975). The technique is well-known and has undergone various refinements and improvements.

General reviews are available in the literature - *Lymphocyte Hybridomas*, ed. Melchers et al., Springer-Verlag (New York 1978), *Methods in Enzymol.* 63 (Part B):3–46 (1981) and *Monoclonal Antibodies*, Plenum Press (1980).

Anti-DNA·RNA antibody-producing lymphocytes may be obtained from various sites, usually the lymph nodes or spleen. Usually, the selected lymphocytes are spleen cells from an animal which has been immunized against the DNA·RNA duplex. Immunization is accomplished by injection of the host animal, e.g., mouse, rat, or goat, at one or more of a variety of sites with an appropriate immunogen conjugate, normally in mixture with an adjuvant. Further injections are made at the same or different sites at regular or irregular intervals thereafter until it is evident that anti-DNA·RNA antibodies are being produced in vivo.

While unconjugated DNA·RNA can be used as the immunogen, it has been found desirable to employ an immunogen complex comprising DNA·RNA bound to a conventional carrier material, most commonly, a protein or polypeptide. The most practical procedure uses a cationic protein or polypeptide with molecular weight between 5,000 and 5,000,000 daltons, preferably between 20,000 and 3,000,000 and more usually between 50,000 and 1,000,000. Particularly useful proteins are albumins, globulins (thyroglobulin is particularly useful), enzymes, hemocyanins, albuminoids, glutelins, and the like. Covalent coupling of the DNA·RNA duplex to the carrier protein can be employed but electrostatic adsorption of the duplex to the protein is satisfactory and simple. The electrostatic adsorption is favored by cationic properties of the carrier protein. Usually proteins are made more cationic by methylation of the carbonyl residues.

Myeloma cells, that is, malignant cells from primary bone marrow tumors, produce immunoglobulins with unknown specificity and have the ability to propagate in vitro. In contrast, individual lymphocytes characterized by the secretion of immunoglobulins with known specificity, i.e., antibodies capable of binding a known antigen or hapten, are labile under in vitro culturing. A hybridoma, i.e., a hybrid cell formed by fusion of a single lymphocyte with a single myeloma cell, retains the desired immunological specificity of the lymphocyte parent cell and the desired in vitro stability of the myeloma parent cell. Myeloma cells of various animal origin can be used according to the present invention, for example, myeloma cells from mice, rats, or man, however, for reasons of genetic stability it is preferred to fuse lymphocytes and myeloma cells derived from the same animal species, and most preferably, from the same strain of such animal species. Murine lymphocytes and myeloma cells are most commonly used, particularly from the BALB/c strain.

Myeloma cells may be of the secreting or nonsecreting type, the former characterized by secretion of immunoglobulin or fragments thereof from the cell into the surrounding medium. Nonsecreting cell lines are preferred since the resulting hybridomas will feature secretion of only the specific immunoglobulin (e.g., IgG, IgE, IgM, IgA or IgD classes) produced by the parent lymphocyte. Moreover, myeloma cells which have been rendered deficient in a particular nucleotide synthetase enzyme are particularly preferred since such a circumstance provides ready means for isolating hybridomas from nonfused lymphocytes and myeloma cells. When grown on a culture medium containing the substrate or substrates for the nucleotide synthetase enzyme in which the myeloma cell is deficient as the only source of nucleotide formation, hybridomas will survive and proliferate since the deficient enzyme will be provided by retained genetic features from the lymphocyte. However, nonfused myeloma cells will die because of enzyme deficiency and nonfused lymphocytes will die due to their inherent in vitro lability. Preferred myeloma cell lines are those deficient in the enzyme hypoxanthine guanine phosphoribosyl transferase (HGPRT) and unable to survive on culture media containing hypoxanthine, aminopterin, and thymidine for nucleotide synthesis [such media being conventionally referred to as HAT media.- *Science* 145:709 (1964)]. Particular myeloma cell lines which are useful in the present method are those known as X63 [*Nature* 256:495 (1975)], NS-I [*Eur. J. Immunol.* 6:292 (1976)], Sp2/O [*Nature* 226:269 (1978)], and X45 [*Cell* 8:405 (1976)].

Fusing of the lymphocyte and myeloma cells to form hybridomas is accomplished by conventional means, usually by mixing the cells in the presence of a fusing agent such as sendai virus or polyethylene glycol (PEG). The mechanism of fusion is generally unknown and yields efficiencies of one hybridoma formed for about every $10^4$ normal cells present. The ratio of number of lymphocytes to myeloma cells is usually greater than one, more usually 5 or more. Since an unscreened population of lymphocytes is made available to the myeloma cells for fusion, resulting hybridomas will express a distribution of varying antibody secretions. A hybridoma clone, i.e., a population of cells having a common single cell origin, which secretes the desired antibody is isolated by conventional techniques. A common technique involves the division of the fusion mixture into a multiplicity of dilute volumes in the expectation that the majority of resulting volumes which contain hybridomas will contain no more than one. Preferably, the individual volumes will comprise a selective culture medium, e.g., the HAT medium mentioned above, in which only hybridomas will survive. Aliquots of the separate culture fluid are removed after an appropriate incubation period and subjected to an assay for the desired antibodies. Many methods are commonly used in this screening step, including immunoassay procedures such as radioimmunoassay or nonisotopic immunoassays of the homogeneous or heterogeneous type. Culture fluids which are positive for the desired antibody are then usually subcloned, such as by further limiting dilution steps, to assure monoclonal isolation and for stability of the desired hybridoma.

The desired monoclonal antibodies can be harvested by several different methods. In one method, the hybridoma clone is cultured in vitro for an appropriate length of time and aliquots of the culture fluid drawn off to provide monoclonal anti-body-rich fractions. Alternatively, the hybridoma clone is injected intraperitoneally in a host animal, usually a mouse, resulting in in vivo tumor growth and accumulation of large amounts of monoclonal antibody in the ascites fluid which can be appropriately tapped to permit removal of anti-body-rich fractions.

A variety of particular techniques can be used to obtain suitable hybridomas which secrete the present antibodies. For example, a DNA·RNA hybrid can be prepared by transcription of $\phi$X174 virion DNA with RNA polymerase as described by Nakazato [*Biochem.* 19:2835 (1980)]. A suitable quantity of the hybrid (e.g., 150 $\mu$g of hybrid in 250 $\mu$L of 20 mM TRIS-HCl buffer, pH 7.4, 1 mM EDTA) is combined with methylated thyroglobulin (e.g., 150 μg in 250 μL water). A precipitate forms and is suspended in TRIS buffer. This mixture is emulsified with an equal volume of Freunds adjuvant. Mice are each immunized with the suspension (e.g., 0.5 ml) and when serum antibody titers to DNA·RNA develop, hybridomas are prepared (e.g., using Sp2/0-Ag14 myeloma cells obtainable from the American Type Culture Collection, Rockville, Md., U.S.A.) and screened for monoclonal antibody specific for DNA·RNA [Stuart et al. *Proc. Natl. Acad. Sci. U.S.A.* 78:3751 (1981), Galfre and Milstein, *Meth. in Enzymol.* 73:1 (1981)].

The cloned hybridomas are propagated in the peritoneal cavity of mice to generate a large quantity of antibody. The ascites fluid is applied to a suitable affinity column [e.g., Affigel-Blue resin (Bio-Rad Laboratories, Richmond, Va., U.S.A.) equilibrated with 10 mM TRIS HCl buffer, pH 8.0, 0.15 M NaCl]. This chromatography removes albumin and the eluted protein which contains the antibody can be further purified, such as by chromatography on DEAE-Sepharose (Pharmacia Fine Chemicals, Piscataway, N.J., U.S.A.). The chromatography can be developed with a linear gradient of 10 mM TRIS-hydrochloride, pH 8.0, to 10 mM TRIS-hydrochloride, pH 8.0, 200 mM NaCl. The major peak of eluted protein will contain the monoclonal antibody free of transferrin and albumin.

The high degree of specificity and affinity of the present monoclonal antibodies confer significant advantages on their use in the analytical detection of DNA·RNA duplexes. A principal use of the antibodies is as detection means in nucleic acid hybridization assays. A wide variety of hybridization formats can make advantageous use of the present antibodies.

DNA·RNA duplexes formed by specific reannealing of a probe polynucleotide and the sequence of interest can be sensitively and specifically detected by binding to the present antibodies. To facilitate detection of resulting binding, the antibody will normally either be labeled with a detectable chemical group and/or be in an immobilized or immobilizable form. Examples of detectable chemical groups that can serve as labels are enzymatically active groups, such as coenzymes, enzyme substrates, enzyme inhibitors, and enzymes themselves, fluorescers, chromophores, luminescers, specifically bindable ligands such as biotin or haptens which are detectable by binding of labeled avidin or labeled anti-hapten antibodies, and radioisotopes. Immobilized antibody normally comprises the antibody bound covalently or noncovalently to a solid support. Immobilizable antibody normally comprises antibody bearing a specific binding site, such as a biotin or hapten group, that will bind to an immobilized form of a binding partner such as avidin or anti-hapten antibody. When the antibody is labeled, other means can be used to immobilize the hybrid so that detection of label associated with the ultimate solid-phase or liquid-phase is mathematically relatable to the presence of the sequence of interest in the sample. The reverse can also be followed, use of the antibody to immobilize hybrids with other means being used to label them. Also, antibody to the hybrid can be both labeled and immobilized or immobilizable such that the antibody serves both functions of labeling and immobilization. Essentially any nucleic acid hybridization format which can make use of an antibody specific for DNA·RNA duplexes can take advantage of the present monoclonal antibodies.

A few particularly attractive hybridization formats are as follows:

(a) Immobilized sample/labeled antibody - Nucleic acids in a liquid test sample are adsorbed or otherwise immobilized onto a support, or nucleic acids in a tissue section are exposed in situ on a slide. Probe is added and immobilized hybrids detected by binding of labeled antibody. See Rudkin and Stollar, *Nature* 265:472 (1977) and commonly assigned U.S. patent application Ser. No. 747,230, filed June 21, 1985.

(b) Immobilized probe/labeled antibody - The test sample is contacted with the probe in an immobilized or immobilizable form (e.g., modified with biotin or hapten groups and immobilizable by binding to immobilized avidin or anti-hapten antibody). Immobilized hybrids ar detected by binding of labeled antibody. See commonly assigned U.S. patent application Ser. No. 707,420, filed Mar. 1, 1985.

(c) Immobilized antibody/labeled antibody - The test sample is contacted with probe, antibody that is labeled, and antibody that is immobilized or immobilizable. The resulting hybrids form a bridge between the two antibodies to form immobilized, labeled hybrids. See commonly assigned U.S. patent application Ser. No. 668,256, filed Nov. 7, 1984.

(d) Dual hybridization - As in known in the art, dual hybrids can be formed when two probes are used that are complementary to mutually exclusive portions of the sequence of interest. One probe serves as detection probe and the other as separation or immobilization probe. To use the present antibody in such a format, one or the other of the probes is selected to form a DNA·RNA hybrid with the sequence of interest and labeled or immobilized/immobilizable antibody is used. The second probe will then be immobilized/immobilizable or labeled as the case may be.

EXAMPLE I

Monoclonal Antibody to DNA·RNA

A. Preparation of the DNA·RNA Antigen

Precautions were taken to reduce RNase contamination in reagents by autoclaving solutions, dissolving heat-labile reagents in autoclaved water and heating glassware at 200° C. overnight.

DNA·RNA was synthesized in vitro using φ174 ssDNA and *E. coli* DNA-dependent RNA polymerase, essentially as described by Nakazato [*Biochemistry* 19:2835 (1980)]. The reaction mixture contained 85 mM TRIS-HCl buffer, pH 8.0; 50 mM KCl; 10 mM dithiotreitol; 10 mM MnCl$_2$; 0.8 mM each of ATP, CTP, GTP and UTP; 120 μg ssDNA and 300 units of DNA-dependent RNA polymerase in a total volume of 2.0 mL. The reaction mixture was incubated at 37° C. for 2 hours and then made 0.3 M in NaCl by adding 5 M NaCl. RNase I was added to a final concentration of 0.5 μg/mL and incubation a 37° C. was continued for 30 minutes. Then proteinase K was added to give 10 μg/mL and the reaction mixture was incubated to 37° C. for an additional 30 min. One volume of 10 mM TRIS-HCl buffer, pH 7.4, 1 mM EDTA was added and the reaction mixture was extracted with phenol. The aqueous phase was precipitated by addition of two volumes of ethanol and allowing the mixture to stand overnight at −15° C. Precipitated DNA·RNA hybrid was washed with 70% ethanol, dried briefly in vacuum and dissolved in 10 mM Tris-HCl buffer, pH 7.4, 1 mM EDTA. The DNA·RNA concentration was determined by the ethidium bromide fluorescence assay using λ DNA as a standard [Morgan et al., *Nucl. Acids Res.* 1:547 (1979)]. The hybrid was stored at −15° C. in small aliquots.

The DNA·RNA hybrid had a density of 1.51 g/cm$^3$ when examined by equilibrium density gradient centrifugation in $Cs_2SO_4$. The same density was reported by Bassel, et al. [*Proc. Natl. Acad. Sci. U.S.A.* 52:796 (1964)].

B. Preparation of Methylated Thyroglobulin

DNA·RNA used for immunization was complexed with methylated thyroglobulin which was prepared as follows. One hundred milligrams of bovine thyroglobulin was combined with 10 mL of anhydrous methanol and 400 μL of 2.5 M HCl in methanol. The mixture was stirred at room temperature for 5 days. The precipitate was collected by centrifugation and washed twice with methanol and twice with ethanol. Then it was dried under vacuum overnight. About 82 mg of dry powder was obtained.

C. Immunization of Mice

The DNA·RNA hybrid was combined in 2:1 (w/w) ratio with methylated thyroglobulin in 10 mM Tris-HCl buffer, pH 7.4, 1 mM EDTA. The cloudy suspension was emulsified with an equal volume of complete Freund's adjuvant for the initial immunization and with incomplete adjuvant for subsequent boosts. Five BALB/c mice were each immunized subcutaneously with 10 μg of hybrid per injection and two mice each were immunized with 25 μg hybrid per injection. The immunizations were repeated on days 14, 21, 28 and 35. The mice were bled retro-ocularly on days 23 and 37. The serums were screened for the presence of antibodies to DNA·RNA by the enzyme immunoassay method described below.

D. Screening of Mouse Antisera

Antibody titers were monitored by an enzyme immunoassay procedure. All incubations were at room temperature. Fifty microliter aliquots of 1× SSC (0.15 M NaCl, 0.015 M sodium citrate, pH 7.0) containing 5 μg/mL of the appropriate single-stranded or double-stranded polynucleotide antigen were measured into wells of microtiter plates and allowed to stand for 2 hours. The wells were washed three times with 20 mM sodium phosphate buffer, pH 7.4, 0.15 M NaCl (PBS), containing 0.5% (w/v) bovine serum albumin (BSA) and 0.5% (v/v) Tween 20. Then 50 μL of the sample to be tested was added and allowed to stand for 30 minutes. The wells were washed as above and 50 μL of peroxidase labeled anti-mouse IgG, diluted 1000-fold in PBS containing 1% BSA, was added and allowed to stand for 30 minutes. Then the wells were washed as above followed by two washes with PBS alone, and 100 μL of freshly prepared substrate was added. The substrate was prepared by dissolving 20 mg of o-phenylenediamine dihydrochloride in 50 mL of 24 mM citric acid, 50 mL sodium phosphate, pH 5.0, and adding 20 μL of 30% hydrogen peroxide ($H_2O_2$).

The enzyme reaction was allowed to proceed for 20 minutes and was stopped by adding 50 μL of 2.5 M $H_2SO_4$. The absorbances at 488 nm were recorded with an ARTEK model 210 ELISA plate reader (Dynatech Laboratories, Alexandria, Va., U.S.A.).

E. Preparation and Selection of Hybridomas

A mouse with a high polyclonal antibody titer to DNA·RNA and relatively low titers to single and double stranded DNA was selected for production of hybridomas.

The spleen from the selected mouse was pressed through a cell selector, the released lymphocytes were collected by centrifugation and suspended in warm 0.83% (w/v) ammonium chloride to lyse the red blood cells. Lymphocytes and myeloma cells (Sp2/0-Agl4, ATCC) were washed separately in serum free Isocove's modified Dulbecco's medium with 20% horse serum (IMDM), and then washed together at 2 lymphocytes per myeloma cell. The pelleted cells were combined with 0.5 mL of 50% polyethylene glycol which was prepared by adding 1.0 g sterile polyethylene glycol reagent, melted, to 1 mL serum free IMDM. The mixture of fused cells was washed and resuspended in IMDM HAT (IMDM containing 0.12 mM hypoxanthine, 0.09 μM aminopterin, 80 mM thymidine) medium supplemented with 10$^5$ peritoneal exudate cells per mL. The cells were plated into five 96-well tissue culture plates with approximately 200 μL of cell suspension per well. At days 3 and 7 post-fusion the cultures were fed fresh IMDM-HAT medium. Ten days after fusion the culture supernatants were screened by the enzyme immunoassay procedure. The cells from positive wells were grown in larger cultures and screened again for antibody production. Selected cultures were subcloned by limiting dilution in five 96-well tissue culture dishes. Cells were plated at concentrations of 10, 5, 2.5, 1.25 and <1 cells per well in IMDM-HAT supplemented with 10$^5$ spleenocytes per mL. Ten to fourteen days later the supernatants were tested for antibodies by the enzyme immunoassay method.

The clones producing antibodies which bound DNA·RNA but not single and double stranded DNA and RNA were used to prepare ascites fluid. Pristane-primed BALB/c mice were injected intraperitoneally with 10$^5$ hybridoma cells and were tapped for ascites fluid 10 to 14 days later.

F. Purification of Monoclonal Antibodies from Ascites Fluid

Antibodies were purified from ascites fluid by HPLC using a LDC/Milton Roy liquid chromatograph equipped with CI-10 integrator (LDC/Milton Roy, Riviera Beach, Calif., U.S.A.). The ascites fluid was dialyzed against 0.01 M potassium phosphate buffer, pH 6.8, centrifuged to remove particulate matter, and passed through a 0.22 μm nitrocellulose filter. One to two milliliters of processed ascites fluid was applied to a 10×250 mm Bakerbond MAb ™ anion-exchange column (J. T. Baker Chemical Co., Phillipsburg, N.J., U.S.A.) equilibrated with 0.01 M potassium phosphate, pH 6.84. The chromatography was developed with a 60 minute linear gradient from 0.01 M potassium phosphate buffer, pH 6.84, to 0.085 M potassium phosphate, pH 6.40, at a flow rate of 1 mL/min. The peak containing IgG was concentrated, dialyzed against PBS, centrifuged to remove any denatured protein, and the IgG concentration was determined on the basis of absorbance at 280 nm using $E_{1\ cm}^{1\ mg/mL} = 1.40$. Purities of antibody preparations were evaluated by sodium dodecylsulfate-polyacrylamide gel electrophoresis [Blattler et al., *J. Chromatography* 64:147–155 (1972)].

EXAMPLE II

Characterization of Monoclonal Antibody to DNA·RNA

A. Preparation of DNA·[$^3$H] RNA

Radiolabeled DNA·[$^3$H] RNA hybrid used in antibody binding studies was prepared by the transcription method described above with the following modifications. During the first 40 minutes of incubation ATP was replaced with 0.03 mM 3H-ATP (53 Ci/mmol). When the reaction mixture had incubated for 40 minutes, unlabeled ATP was added to give 0.8 mM final concentration and the incubation was continued as described for preparation of the unlabeled hybrid. After the phenol extraction and ethanol precipitation, DNA·$^3$H-RNA was separated from unincorporated nucleotides by chromatography on 10 mL column of Sephadex G-50 (Pharmacia, Piscataway, N.J., U.S.A.) in 10 mM TRIS-HCl buffer, pH 7.4, 1 mM EDTA, containing 0.3 M NaCl. The peak containing DNA [$^3$H] RNA was pooled and the concentration of the hybrid was determined by the ethidium bromide fluorescence assay (Morgan et al., supra). The specific activity of the labeled hybrid was approximately $4 \times 10^6$ cpm/$\mu$g.

B. Antibody Binding Measurements with Radiolabeled DNA·RNA Hybrid

Reactions involving antibody binding to DNA·[$^3$H] RNA and other polynucleotides were performed at room temperature in 1.5 mL polypropylene micro test tubes in 0.5 mL of 20 mM sodium phosphate buffer, pH 8.0, 0.15 mM NaCl, (PBS, pH 8.0), containing 10. $\mu$g BSA/mL. The reaction mixtures were allowed to stand for 30 minutes and then 100 $\mu$L of Pansorbin [Protein A on S. aureus cells available from Behring Diagnostics, LaJolla, Calif., U.S.A.] diluted 50-fold in PBS, pH 8.0, was added and the mixtures were agitated gently by rotating the tubes end over end for 60 minutes. Then the mixtures were centrifuged at 3000 $\times$ g for 4 minutes and 500 $\mu$L aliquots of the supernatants were added to 5.0 mL scintillation fluid for measurement of radioactivity. Bound radioactivity was determined from the difference between total radioactivity added and that measured in the supernatants, after correction for nonspecific binding obtained in control reactions with equivalent levels of non-immune rabbit IgG.

In some assays the separation of free from bound DNA [$^3$H] RNA was accomplished by filtration of the reaction mixtures through 0.45 $\mu$m average pore size nitrocellulose membranes. The antibody binding was conducted in 1 mL of PBS, pH 8.0, containing 10 $\mu$g BSA/mL in $10 \times 75$ mm glass test tubes. The mixtures were allowed to stand at room temperature for 30 minutes and then were filtered through nitrocellulose membranes. The filters were washed twice with 4 mL of $1 \times$ SSC and once with 4 mL H$_2$O, dried, placed in 5.0 mL scintillation fluid, and the radioactivity was measured. Tritium associated with the membranes was used to estimate the antibody bound DNA·[$^3$H] RNA.

C. Affinity

The monoclonal antibodies were screened initially for those with highest affinity. Characteristics of one high affinity antibody are outlined below. The examined antibody was obtained from a hybridoma that has been deposited with the American Type Culture Collection, Rockville, Md., U.S.A., and designated ATCC HB 8730.

The affinity of the antibody was measured by Scatchard analysis using protein A to separate bound and free DNA·[$^3$H] RNA. The data were fitted to the equation:

$$\frac{[B]}{[F]} = K(n[Ab] - [B])$$

where [B] and [F] are molar concentrations of bound and free DNA·RNA respectively, [Ab] is the antibody concentration, n is two, the number of binding sites per antibody and K is the association constant. This model assumes that the two antibody binding sites function independently. FIG. 1 shows plots of [B]/[F] versus [B] obtained with two levels of the antibody. The reaction mixtures contained 0.5 ng (points represented by closed circles) or 1.0 ng (closed triangles) of IgG and increasing concentrations (0.35 to 8 ng with 0.5 ng antibody; 0.7 to 16 ng with 1.0 ng antibody) of DNA·RNA in 0.5 mL PBS, pH 8.0, containing 10 $\mu$g/mL bovine serum albumin. Bound and free antigens were separated with Pansorbin. Each point is an average of two independent experiments, each with triplicate measurements. The data are linear within experimental error and the lines for the two levels of antibody are nearly parallel. The slopes are $1.9 \times 10^{12}$ L/mole at 0.5 ng antibody and $2.2 \times 10^{12}$ L/mole at 1.0 ng.

[B] and [F] were calculated assuming that the $\phi$X174 ssDNA was completely transcribed and that the product had 5400 base pairs. The intercept on the abscissa in FIG. 1 gives the amount of DNA·RNA required to saturate the antibody binding sites. The antibody/DNA·RNA molar ratios, R, calculated at saturation were 11 and 13 at 0.5 and 1.0 ng antibody, respectively. Creighton [Biochem. 20:4308 (1980)] defines the association constant, K', for multivalent ligands as:

$$K' = \frac{C}{(A - C)(L - C)}$$

where A is total antibody binding site concentration, L is total ligand binding site concentration and C is the concentration of antibody-antigen complex. Following this definition each DNA·RNA hybrid was nR binding sites and the values of [B] and [F] should be increased by this factor. Then the observed association constant calculated at 0.5 and 1.0 ng antibody becomes $8.5 \times 10^{10}$ L/mole The filter assay was also employed for separation of antibody bound and free DNA·[$^3$H] RNA. Although the precision was not as good as that obtained with the protein A method, results of several experiments gave antibody/DNA·RNA ratios similar to the protein A method. The association constants also agreed within experimental error.

Binding results obtained with two other antibodies were virtually the same as those obtained for the antibody examined above.

D. Specificity

Figure 2:
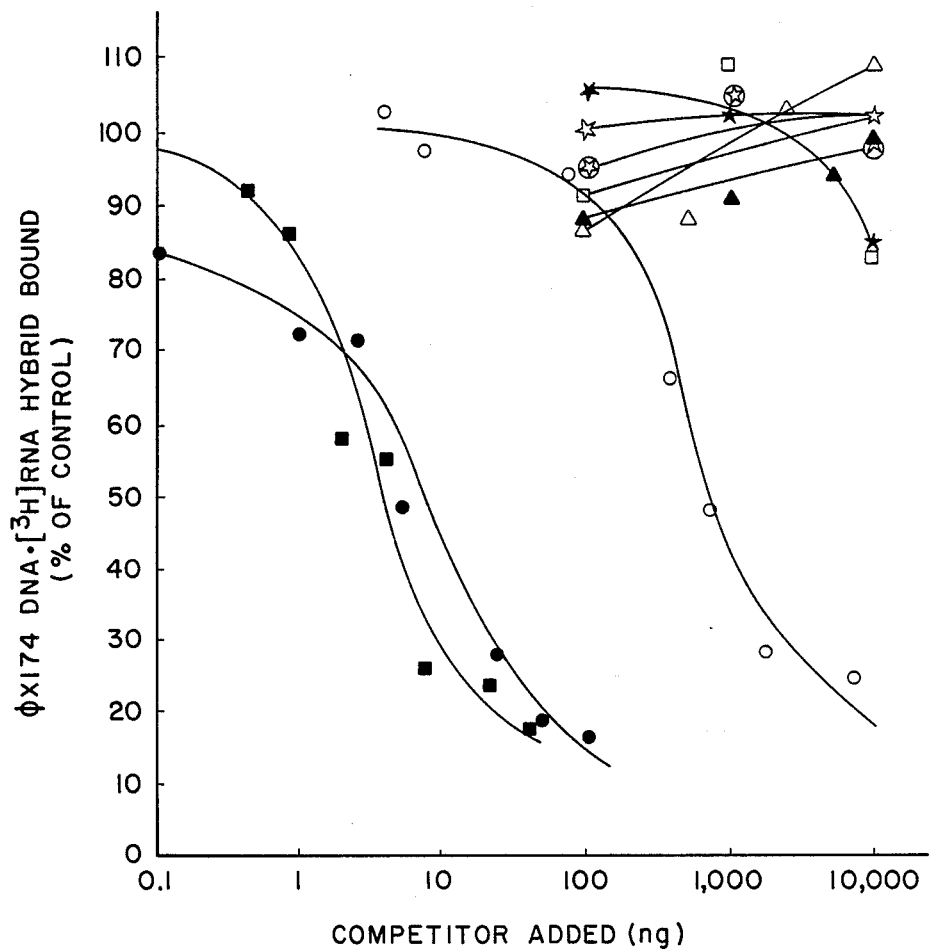
FIG. 2 is a graphical representation of the specificity of the present antibody for DNA·RNA duplexes, particularly DNA·RNA heteropolymers. The curve whose points are represented by closed circles shows binding to DNA·RNA heteropolymer, while closed squares and open circles curves show binding to the DNA·RNA homopolymers poly(I)·poly(dc) and poly(A)·poly(dT), respectively. The remaining curves show the substantial ineffectiveness of various single- and double-stranded DNA and RNA hetero- and homopolymers for binding to the antibody. Details are provided in Example II.

The specificities of the preferred monoclonal antibody was evaluated by a competitive immunoassay method. Various levels of potential competitors were combined with the DNA·[$^3$H] RNA antigen and binding reactions were initiated by the addition of antibody at a level which bound 40-60% of the hybrid. Each reaction had 4 ng DNA·[$^3$H] RNA and 3 ng antibody. Results are averages of triplicate measurements and are corrected for nonspecific binding to Pansorbin. The following polynucleotides were tested: the unlabeled DNA·RNA transcription product (curve drawn through points represented by closed circles), poly(I)·poly(dC) (closed squares), poly(A)·poly(dT) (open circles), $\lambda$ phage ds-DNA (open triangles), $\phi$174 ss-DNA (stars in closed circles), E. coli ribosomal RNA (closed triangles), $\phi$16 ds-RNA (open stars), poly(I)·poly(C) (closed stars), and poly(A)·poly(U) (open squares). The antibody bound poly(I)·poly(dC) as strongly as the unlabeled DNA·RNA heteropolymer (FIG. 2). Poly-(A)·poly(dT) was also an effective competitor but only at levels about 100-fold above those used for the unlabeled DNA·RNA. The other polynucleotides were ineffective competitors even at levels more than 10,000-fold above the unlabeled DNA·RNA heteropolymer.

The above examples provide representative embodiments of the present invention. Obviously many other embodiments can be made without departing from the inventive features of the subject matter claimed below.

What is claimed is:

1. The monoclonal antibody secreted by hybridoma cell line ATCC HB 8730.
2. Hybridoma cell line ATCC HB 8730.